United States Patent
Moses

(10) Patent No.: US 9,795,634 B1
(45) Date of Patent: Oct. 24, 2017

(54) DRUG DELIVERY SYSTEMS AND METHODS FOR TREATING CANCER USING GOLD NANOPARTICLES COATED WITH CITRATE IONS, FRANKINCENSE AND MYRRH

(71) Applicant: Sherita L. Moses, Huntsville, AL (US)

(72) Inventor: Sherita L. Moses, Huntsville, AL (US)

(73) Assignee: Alabama A&M University, Huntsville, AL (US)

( * ) Notice: Subject to any disclaimer, the term of this patent is extended or adjusted under 35 U.S.C. 154(b) by 0 days.

(21) Appl. No.: 15/051,977

(22) Filed: Feb. 24, 2016

Related U.S. Application Data

(60) Provisional application No. 62/120,315, filed on Feb. 24, 2015, provisional application No. 62/288,910, filed on Jan. 29, 2016.

(51) Int. Cl.
  *B82Y 30/00* (2011.01)
  *A61K 33/24* (2006.01)
  *A61K 9/51* (2006.01)
  *A61K 9/00* (2006.01)

(52) U.S. Cl.
  CPC ............ *A61K 33/24* (2013.01); *A61K 9/0019* (2013.01); *A61K 9/5176* (2013.01); *B82Y 30/00* (2013.01)

(58) Field of Classification Search
  CPC ............................. B82Y 30/00; A61K 9/0019
  See application file for complete search history.

(56) References Cited

PUBLICATIONS

"Gold, Frankincense and Myrrh", Cancer Research UK, Dec. 2007.*

Cai, W., Gao, T., Hong, H., Sun, J. (2008). Applications of gold nanoparticles in cancer nanotechnology. Nanotechnology, Science and Applications, 1, 17-32.

Chen, Y., Zhou, C., Ge, Z., Liu, Y., Liu, Y., Feng, W . . . Wei, T. (2013). Composition and potential anticancer activities of essential oils obtained from myrrh and frankincense. Oncology Letters, 6 (4), 1140-1146.

Dume, B. (2013). Positive or negative? Nanoparticle surface charge affects cell membrane interactions. Physics World. Published Jun. 7, 2013. 2 pages.

El-Sherbiny, I., Salih, E., Reicha, F. (2012). Green synthesis of densely dispersed and stable silver nanoparticles using myrrh extract and evaluation of their antibacterial activity. Journal of Nanostructure in Chemistry, 3:8.

Faraji, A., Wipf, P. (2009). Nanoparticles in drug delivery. Bioorg Med Chem, 17 (8): 2950-2962.

Frank, M, Yang, Q., Osban, J., Assarello, J., Saban, M., Saban, R., Welter, J. (2009). Frankincense oil derived from Boswellia carteri induces tumor cell specific cytotoxicity. BMC Complementary and Alternative Medicine, 9:6.

(Continued)

*Primary Examiner* — Carlos Azpuru
(74) *Attorney, Agent, or Firm* — Maynard Cooper & Gale, P.C.; Jon E. Holland

(57) ABSTRACT

The present disclosure generally pertains to systems and methods for the treatment of cancer. Disclosed herein are compositions for the treatment of cancer, such compositions comprising a plurality of gold nanoparticles coated with citrate ions, frankincense and myrrh. Also disclosed herein are methods for the treatment of cancer, such methods comprising the administration of a plurality of gold nanoparticles coated with citrate ions, frankincense and myrrh.

10 Claims, 12 Drawing Sheets

(56) References Cited

PUBLICATIONS

Laszczyk M. (2009). Pentacyclic triterpenes of the lupane, oleanane and ursane group as tools in cancer therapy. Planta Med, 75 (15), 1549-1560.

Moghimi, S., Szebeni, J. (2003). Stealth liposomes and long circulating nanoparticles: critical issues in pharmacokinetics, opsonization and protein-binding properties. Progress in Lipid Research, 42, 463-478.

Ngwa, W., Kumar, R., Sridhar, S., Korideck, H., Zygmanski, R., Cormack, A., Makrigiorgos, G. (2014). Targeted radiotherapy with gold nanoparticles: current status and future perspectives. Nanomedicine, 9(7), 1063-1082.

Paciotti, G., Myer, L., Weinreich, D., Goia, D., Pavel, N., Mclaughlin, R., Tamarkin, L. (2004). Colloidal gold: a novel nanoparticle vector for tumor directed drug delivery. Drug Deliv, 11, 169-183.

Perrault, S., Walkey, C., Jennings, T., Gischer, G., Chan, W. (2009). Mediating tumor targeting efficiency of nanoparticles through design. Nano Letters 9(5), 1909-1915.

Rafi, M, Ho, C. (2001). Gift of the magi bears anti-cancer agents, researchers suggest. American Chemical Society, published in Science Daily Dec. 5, 2001. 3 pages.

Raghunandan, D., Ravishankar, B., Sharanbasava, G., Hahesh, D., Harsoor, V., Yalagatti, M., Venkataraman, A. (2011). Anti-cancer studies of noble metal nanoparticles synthesized using different plant extracts. Cancer Nano, 2:57-65.

Selim, M., Hendi, A. (2012). Gold nanoparticles induce apoptosis in MCF-7 human breast cancer cells. Asian Pacific Journal of Cancer Prevention, 13(4): 1617-1620.

Su, S., Wang, T., Chen, T., Duan, J., Li, Y., Tang, Y. (2011). Cytotoxicity activity of extracts and compounds from Commiphora myrrha resin against human gynecologic cancer cells. Journal of Medicinal Plants Research. 5 (8), 1382-1389.

Suhail, M., Wu, W., Cao, A., Mondalek, F., Fung, K., Shih, P., Lin, H. (2011). Boswellia sacra essential oil induces tumor cell specific apoptosis and suppresses tumor aggressiveness in cultured human breast cancer cells. BMC Compl and Alternative Medicine, 11, 129.

Turkevich, J., Stevenson, P., Hillier, J. (1951). A study of the nucleation and growth processes in the synthesis of colloidal gold. Discussions of the Faraday Society, 11, 55-75.

Kimling, J., Maier, M., Okenve, B., Kotaidis, V., Ballot, H., Plech, A. (2006). Turkevich method for gold nanoparticle synthesis revisited. J Phys Chem B, 110, 15700-15707.

U.S. Appl. No. 62/288,910, entitled "Drug Delivery Systems and Methods for Treating Cancer", filed Jan. 29, 2016.

U.S. Appl. No. 62/120,315, entitled "Drug Delivery Systems and Methods for Treating Breast Cancer", filed Feb. 24, 2015.

\* cited by examiner

Untreated MDA-MB-231

MDA-MB-231 Control

0.1% MDA-MB 231 Regular Strength

0.1% MDA-MB-231 Extra Strength

Untreated MCF-7

MCF-7 Control　　　0.1% MCF-7　　　0.1% MCF-7

Regular Strength　Extra Strength

MCF-10A Regular Strength (UH)    MCF-10A Extra Strength (UH)

DRUG DELIVERY SYSTEMS AND METHODS FOR TREATING CANCER USING GOLD NANOPARTICLES COATED WITH CITRATE IONS, FRANKINCENSE AND MYRRH

CROSS REFERENCE TO RELATED APPLICATIONS

This application claims priority to U.S. Provisional Patent Application No. 62/120,315, entitled "Drug Delivery Systems and Methods for Treating Breast Cancer" and filed on Feb. 24, 2015, and to U.S. Provisional Patent Application No. 62/288,910, entitled "Drug Delivery Systems and Methods for Treating Cancer" and filed on Jan. 29, 2016, which are both incorporated herein by reference.

BACKGROUND

Conventional treatments for cancer, such as chemotherapy and radiation therapy, can be used to selectively kill rapidly dividing cancer cells in the body. Conventional treatments, however, exhibit poor target specificity. The efficacy of chemotherapy, for example, is hindered, because chemotherapeutic agents affect both cancerous and non-cancerous rapidly dividing cells. The efficacy of chemotherapy is further decreased by poor retention of the chemotherapeutic agents within the target tumors.

Unfortunately, because conventional therapies also affect non-cancerous rapidly dividing cells, hair follicles, mucosal cells and hematopoietic cells are affected. As a result, conventional treatments for cancer typically result in undesirable, often severe, side effects including, but not limited to, hair loss, nausea, weight loss, reduction in white blood cells and damage to the mucosa. The suffering that cancer patients must endure results in a stressful course of therapy and may reduce patient compliance with prescribed therapies. Further, some cancers defy currently available treatment options, despite improvements in disease detection.

Unfortunately, therapies that specifically target and disrupt cancerous cells without harming non-cancerous cells, and therefore reducing or eliminating the unwanted side effects of conventional therapies, remain elusive.

BRIEF DESCRIPTION OF THE DRAWINGS

The present disclosure can be better understood with reference to the following figures.

DETAILED DESCRIPTION

The present disclosure generally pertains to systems and methods for the treatment of cancer. Disclosed herein are compositions for the treatment of cancer, such compositions comprising a plurality of gold nanoparticles coated with citrate ions, frankincense and myrrh. Also disclosed herein are methods for the treatment of cancer, such methods comprising the administration of a plurality of gold nanoparticles coated with citrate ions, frankincense and myrrh.

The use of any and all examples, or exemplary language ("e.g.," "such as," or the like) provided herein, is intended merely to better illuminate the embodiments and does not pose a limitation on the scope of the embodiments.

As used herein, "coated with" means a surface in which one or more compounds are affixed to, adsorbed on, conjugated to, bonded to, or otherwise adhered to, such surface.

As used herein, "frankincense" means extracts obtained from *Boswellia sacra*. Alternate forms of frankincense are also contemplated, including extracts from other species of plants from which frankincense may be extracted, as known in the art.

As used herein, "myrrh" means extracts obtained from *Commiphora myrrha*. Alternate forms of myrrh are also contemplated, including extracts from other species of plants from which myrrh may be extracted, as known in the art.

As used herein, "subject" means a human. Alternate subjects are also contemplated, including animals.

As used herein, "Aura-Bosphora" (ABP) means compositions of AuNPs, reduced and capped, and coated with frankincense and myrrh.

The present disclosure contemplates compositions including a plurality of gold nanoparticles (AuNPs), each reduced and capped, and coated with frankincense and myrrh. In certain embodiments, the composition is suspended in a solution at physiological pH. In certain embodiments, the gold nanoparticles have diameters less than about 30 nm. In other embodiments, the gold nanoparticles have diameters ranging between about 10 nm and 20 nm.

Figure 1:
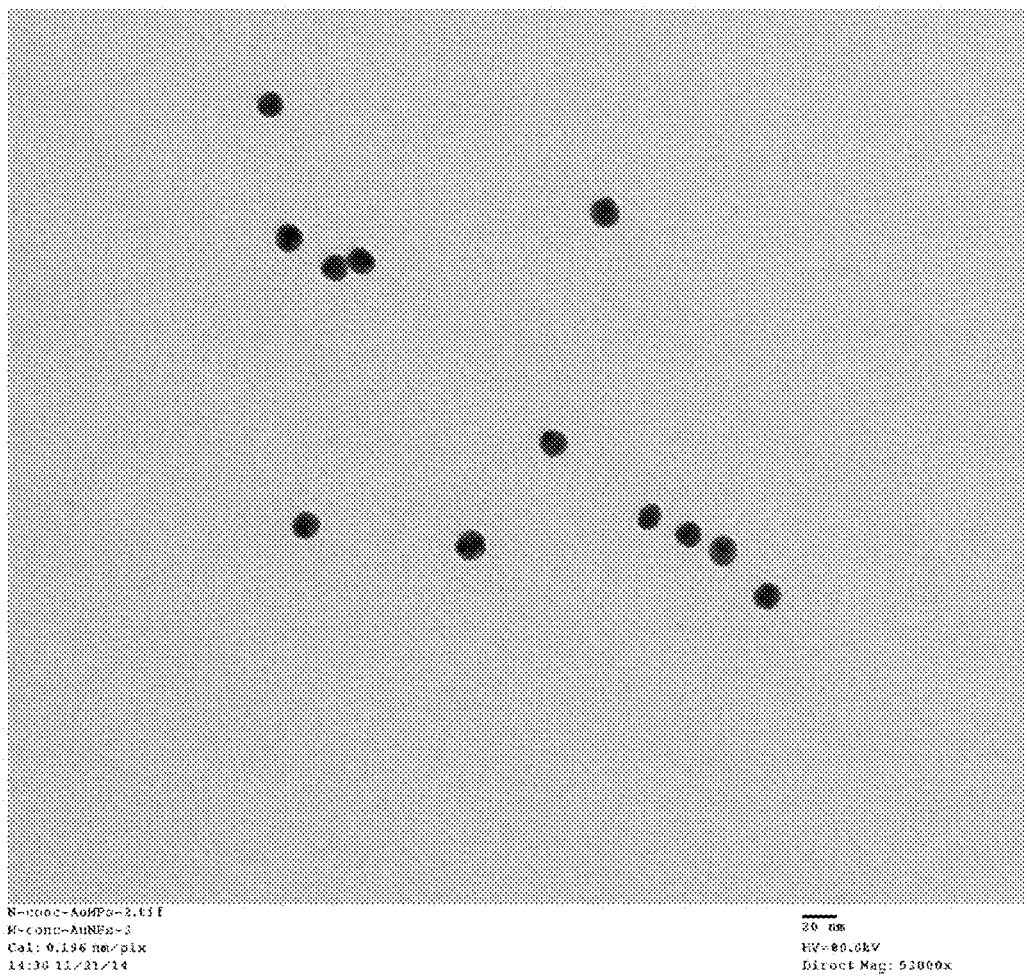
FIG. 1 is a photograph showing monodispersed gold nanoparticles approximately 15-20 nm in diameter.

In certain embodiments, the surfaces of AuNPs may be reduced and "capped" using the Turkevich/Frenz Method to prevent aggregation. The use of such method will coat the AuNPs using trisodium citrate dihydrate (TSCD) to coat the surface of the AuNPs with citrate ions, which hold a negative charge, causing them to repel, preventing aggregation in the blood stream of a subject, and allowing smoother flow throughout a subject. An exemplary embodiment of monodispersed AuNPs, having diameters between approximately 15-20 nm and capped with citrate ions, is depicted in FIG. 1. In other embodiments, the AuNPs are reduced and capped using other methods known in the art.

The composition includes AuNPs coated with frankincense and myrrh. In certain embodiments, the frankincense is an extract of *Boswellia sacra*. In certain embodiments, the myrrh is an extract of *Commiphora myrrha*. In certain embodiments, the frankincense and myrrh are therapeutic grade essential oils.

In certain embodiments, the frankincense comprises: Boswellic acid; at least one sesquiterpene; incensole acetate; alpha-pinene; limonene; myrcene; beta-phellandrene; benzene; alpha-phellandrene; 1,3,6 heptatriene; and cycloalkane. As used herein, Boswellic acid includes, but is not limited to, acetyl-Boswellic acid, beta-Boswellic acid, acetyl-beta-Boswellic acid, 11-Keto-beta-Boswellic acid, and/or acetyl-11-keto-beta-Boswellic acid and other forms of Boswellic acid known in the art.

In certain embodiments, the myrrh comprises: furanocudesma-1, 3-diene; curzarene; nitrofurantoin; diethyl phthalate; 2-ethoxy-6-ethyl-4,4,5 trimethyl-1,3 dioxa-4 sila-2 boracylcohex-5-ene; and napthalene. In certain embodiments, the myrrh comprises at least one sesquiterpene. As used herein, the term sesquiterpene includes furanocudesma-1, 3-diene, curzarene, and other sesquiterpenes known in the art.

In certain embodiments, the present disclosure contemplates a method of treating cancer in a subject by administration of Aura-Bosphora. In certain embodiments, the cancer in a subject is breast cancer. In certain embodiments, Aura-Bosphora may be administered to a subject by direct injection into a tumor site. In certain embodiments, Aura-Bosphora may be administered to a subject by direct injection into a tumor microenvironment. In other embodiments, Aura-Bosphora may be administered to a subject by intravenous injection. In other embodiments, Aura-Bosphora may be administered to a subject by intraperitoneal injection.

EXAMPLES

Citrate-Reduced AuNP Production

Figure 2:
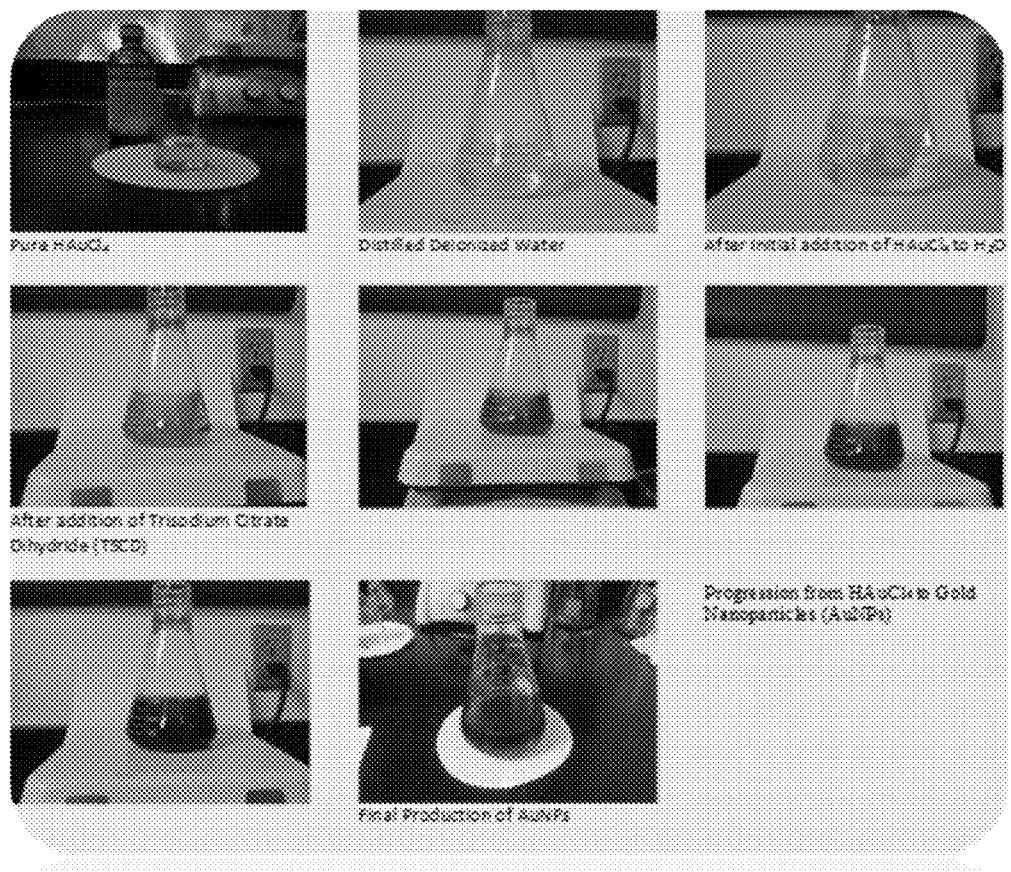
FIG. 2 is a sequence of photographs depicting the production of gold nanoparticles.

Single phase water based reduction of gold by citrate (the Turkevich/Frenz Method) was used. 20 ml of $HAuCl_4$ were added to 100 ml of purified, distilled, deionized water and heated to 80° C., while constantly stirred with a magnetic stirrer. 0.2 g of trisodium citrate dihydrate (TSCD) was added to the aqueous solution and brought to a rolling boil at 100° C. The solution continued to boil until the color changed from pale yellow, to lavender, to purple, then to ruby red (approximately 14-15 minutes), indicating the presence of gold nanoparticles (the "control" solution), as depicted in FIG. 2.

This procedure was repeated, the solution was then cooled to room temperature, 15 ml of *Boswellia sacra* extract and 15 ml of *Commiphora myrrha* extract were added to the gold particle solution and magnetically stirred for 30 minutes to produce the "regular strength" composition.

This procedure was repeated, and 30 ml of *Boswellia sacra* extract and 30 ml of *Commiphora myrrha* extract were added to the gold nanoparticle solution producing the "extra strength" composition. Both compositions were stored at 5° C. in amber glass bottles.

*Boswellia sacra* and *Commiphora myrrha* extracts were purchased from Native American Nutritionals, where the distilling process used both $CO_2$ and hydrodistillation to obtain the essential oils which are 100% pure, exceptional therapeutic grade.

UV-VIS Spectroscopy Analysis of AuNP

Figure 3:
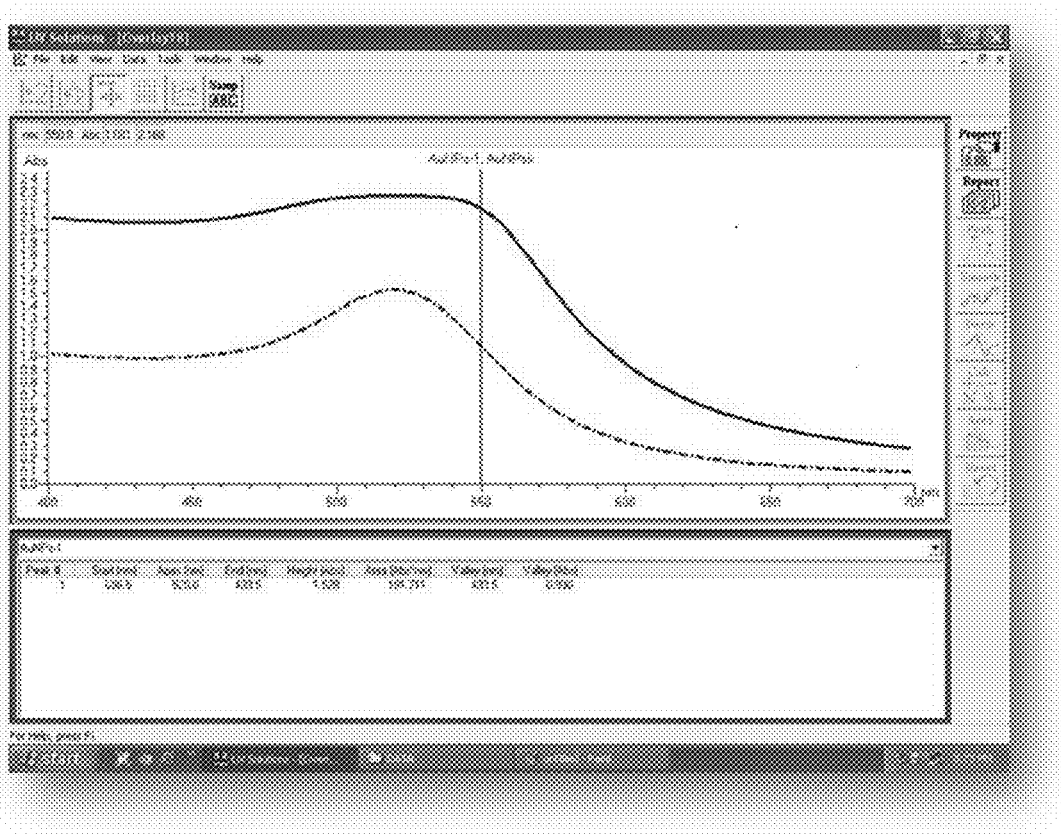
FIG. 3 shows UV-Vis Spectrometer results confirming presence of small AuNPs, 10-20 nm in diameter in both the regular strength compound (bottom curve) as well as the extra strength compound (top curve).

To confirm the presence of gold nanoparticles, the solution was analyzed on the UV-Visible Spectrometer, as shown in FIG. 3, to quantify the light absorbed and scattered by the gold nanoparticles. The data were then plotted as extinction as a function of wavelength. The presence of gold nanoparticles was confirmed, with the data revealing the characteristic wavelength for gold nanoparticles ranging from 10-20 nm is 520 nm.

The synthesized nanoparticles showed an intense localized surface plasmon resonance absorption band at 520 nm. This absorption band centered at approximately 520 nm is characteristic of gold nanoparticles and is due to the surface plasmon resonance absorption which gives rise to the gold nanoparticle's red color. For small (~30 nm) monodispersed gold nanoparticles, the surface plasmon resonance phenomena causes an absorption of light in the blue-green portion of the spectrum (~450 nm) while red light (~700 nm) is reflected, yielding a rich red color (Gold Nanoparticles). The absorption maximum increases from 520 nm to 570 nm for 20 nm and 100 nm spherical gold nanoparticles, respectively (Gold Nanoparticle Properties). Typically, gold nanospheres show a single absorption peak in the visible range between 510-550 nm because of surface plasmon resonance, and show heavy absorption of visible light at 520 nm.

Gas Chromatograph Mass Spectrometry

Gas Chromatograph Mass Spectrometry, using a Perkin-Elmer GC-MS Clarus 500, was performed to identify the components of the *Boswellia sacra* and *Commiphora myrrha* extracts. Elite 5 MS Column with a length of 20 m and internal diameter of 0.18μ was used. The software used for analysis was Turbo Mass, Wiley Access Mass Spectral Browser 3.2.2 and NIST MS Search 2.0 along with the Wiley Registry of Mass Spectral Data, NIST/EPA/NIN Mass Spectral Library and SDBS Database.

Compounds were identified by comparing their mass spectra with those of the National Institute of Standards and Technology (NIST) library. The results of the analysis are listed in Table 1, which shows that the major components of frankincense (BS) were alpha-pinene, limonene, and myrcene, whereas the major components of myrrh (CM) were nitrofurantoin and diethyl phthalate.

TABLE 1

GC-Mass Spectrometry of *Boswellia sacra* and *Commiphora myrrha* showing area (% covered data).

| Boswellia sacra | AREA (%) | Commiphora myrrha | AREA (%) |
| --- | --- | --- | --- |
| Alpha-Pinene | 44.72 | Nitrofurantoin | 36.55 |
| Limonene | 13.35 | Diethyl Phthalate | 41.12 |
| Myrcene | 8.16 | 2-ethoxy-6-ethyl-4,4,5 trimethyl-1,3 dioxa-4 sila-2 boracyclohex-5-ene | 2.51 |
| Beta-Phellandrene | 5.73 | Naphthalenes | Approx. 8% |
| Benzene | 3.98 | Other Trace Chemicals | |
| Alpha-Phellandrene | 3.83 | | |
| 1,3,6 Heptatriene | 3.23 | | |
| Cycoalkanes | Approx. 5% | | |
| Other Trace Chemicals | | | |

Treatment of Cancer Cells Using AuNPs In Vitro

Human MDA-MB-231 and MCF-7 breast cancer cell lines as well as human MCF-10A breast epithelial cells were obtained from the NCI-Frederick Cancer DCTD tumor/cell line repository. Cells were cultured in RPMI-1640 medium containing 10% FBS (Hyclone, Logan, Utah), 2 mM glutamine and penicillin-streptomycin antibiotic (Mediatech, Herndon, Va.). The MCF-10A cells were cultured in Dulbecco's Modified Eagle's Medium/nutrient mixture F-12 (Mediatech, Herndon, Va.) supplemented with hydrocortisone (Sigma-Aldrich, St. Louis, Mo.), human recombinant EGF (Sigma-Aldrich, St. Louis, Mo.), 5% (v/v) horse serum (Invitrogen, Carlsbad, Calif.), cholera toxin (Calbiochem, BD Biosciences, La Jolla, Calif.) and penicillin-streptomycin antibiotic (Mediatech). Before use, the AuNP compounds were diluted in complete RPMI medium such that the final percentage was no more than 10%, and serial dilutions were made. Alamar Blue™ dye was purchased from BioSource International, (Camarillo, Calif.). All other reagents were purchased from Sigma Aldrich.

The ability of the gold nanoparticle and gold nanoparticle mixtures to impact the viability of MDA-MB-231, MCF-7 and MCF-10A cells was determined using the Alamar Blue™ assay as previously described. Cells were plated in 96-well plates at their appropriate densities (2-5,000 cells/well) in a total volume of 100 microliters. After 24-48 hours of incubation, cells were treated with 10% gold nanoparticle in buffer (control) or gold nanoparticle compound with extracts (regular strength or extra strength) for 72 hours before the addition of 10 microliters of Alamar Blue™ dye. After 4 hours of dye incubation, the plates were read using an FLx800 microplate fluorescence reader (excitation and emission=530 and 590 nm respectively). Following the 72 hour incubation, cells were visualized using relief contrast microscopy.

Figure 4:
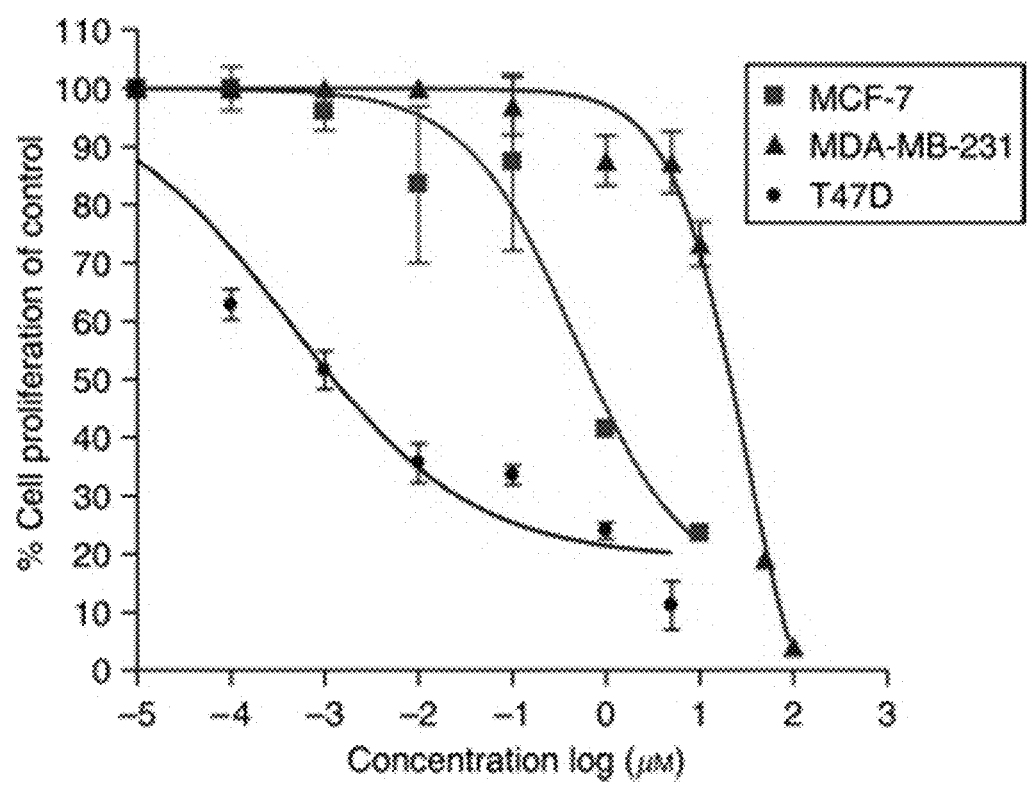
FIG. 4 is a chart depicting sample data from plated cells.
Figure 5:
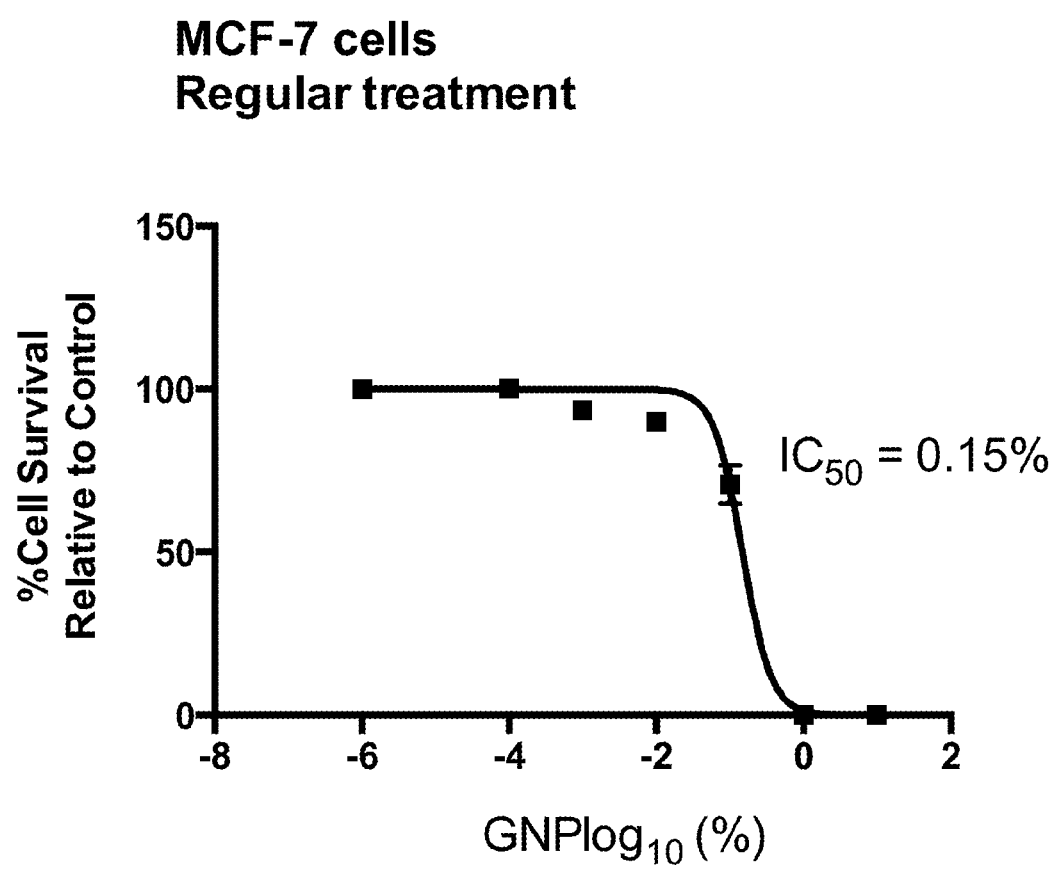
FIG. 5 is a graph depicting the concentration of an exemplary gold nanoparticle composition necessary for 50% inhibition of the proliferation of MCF-7 cancer cells in vitro.

Apoptotic body formation was observed in cells exposed using an Olympus IX71 inverted microscope with relief contrast imaging. Images were captured using a SPOT digital camera system. MCF-10A, MDA-MB-231 and MCF-7 cells were plated in 96-well plates and allowed to attach overnight. The cells were then exposed to gold nanoparticles in buffer (control) or gold nanoparticle compound with extracts at both strengths for 72 hours, and then imaged to determine proliferation (as shown in FIG. 4) and dose response curves.

The dose response curves were plotted, and using a curve-fitting program the percentage of the given mixtures that were able to cause a reduction in cell viability by 50% ("$IC_{50}$") was determined, as shown in FIGS. 5-9. The cells were exposed to the compounds for 72 hours before performing the Alamar Blue assay. In addition, cells were visualized using relief contrast microscopy. Cells exposed to gold nanoparticles alone served as the control in comparison to percent mixtures near the $IC_{50}$ values determined for both "regular" and "extra strength" AuNP compositions (as described in paragraphs 32 and 33).

Figure 6:
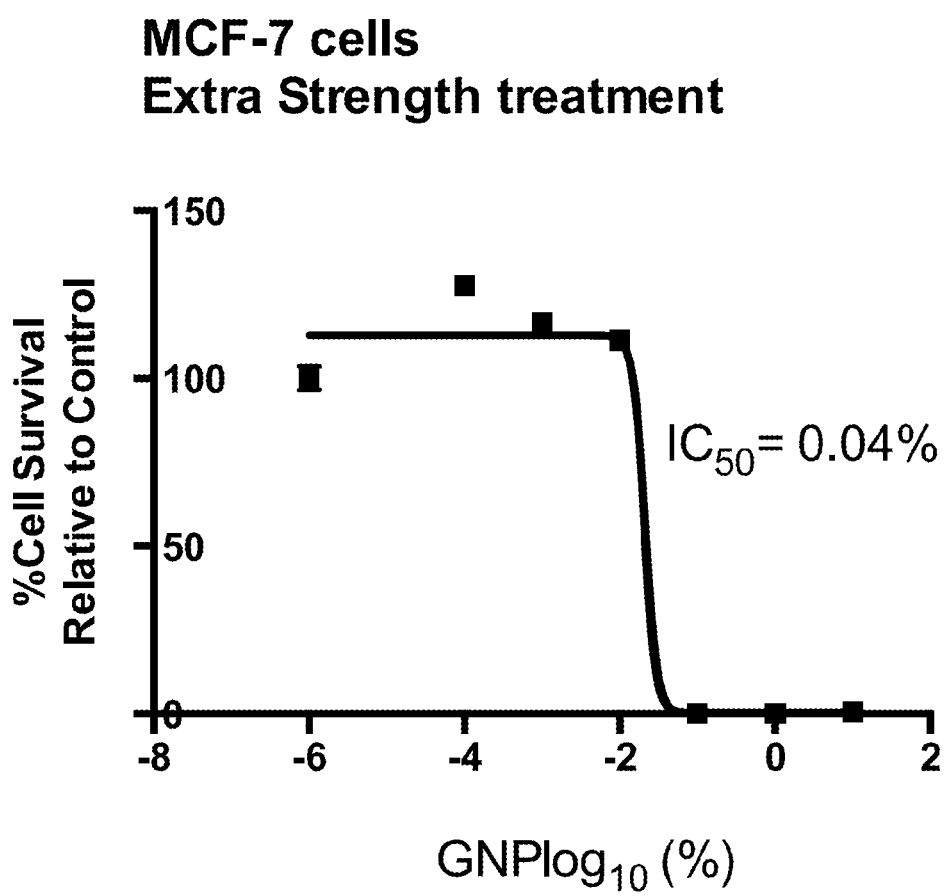
FIG. 6 is a graph depicting the concentration of an exemplary gold nanoparticle composition necessary for 50% inhibition of the proliferation of MCF-7 cancer cells in vitro.

For the regular strength composition, the percentage needed to diminish the growth of MCF-7 cells by at least 50% was approximately 0.15% (FIG. 5) and for the extra strength composition, the percentage was approximately 0.04% (FIG. 6). The composition displayed even more activity in the aggressive MDA-MB-231 cells compared with the less aggressive MCF-7 cells.

Figure 7:
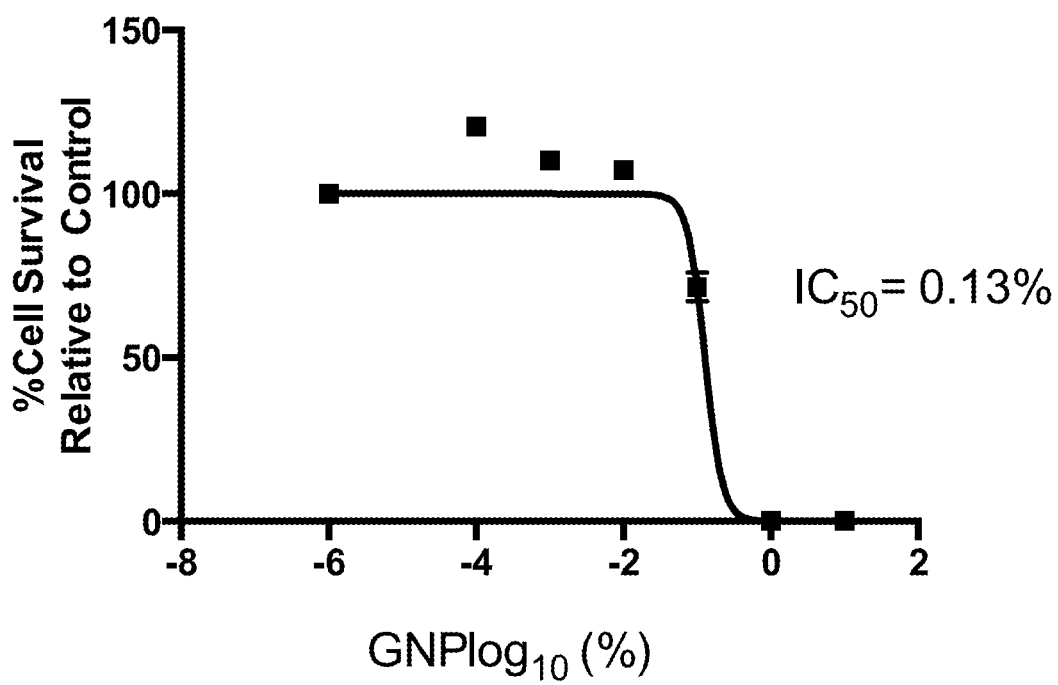
FIG. 7 is a graph depicting the concentration of an exemplary gold nanoparticle composition necessary for 50% inhibition of the proliferation of MDA-MB-231 cancer cells in vitro.
Figure 8:
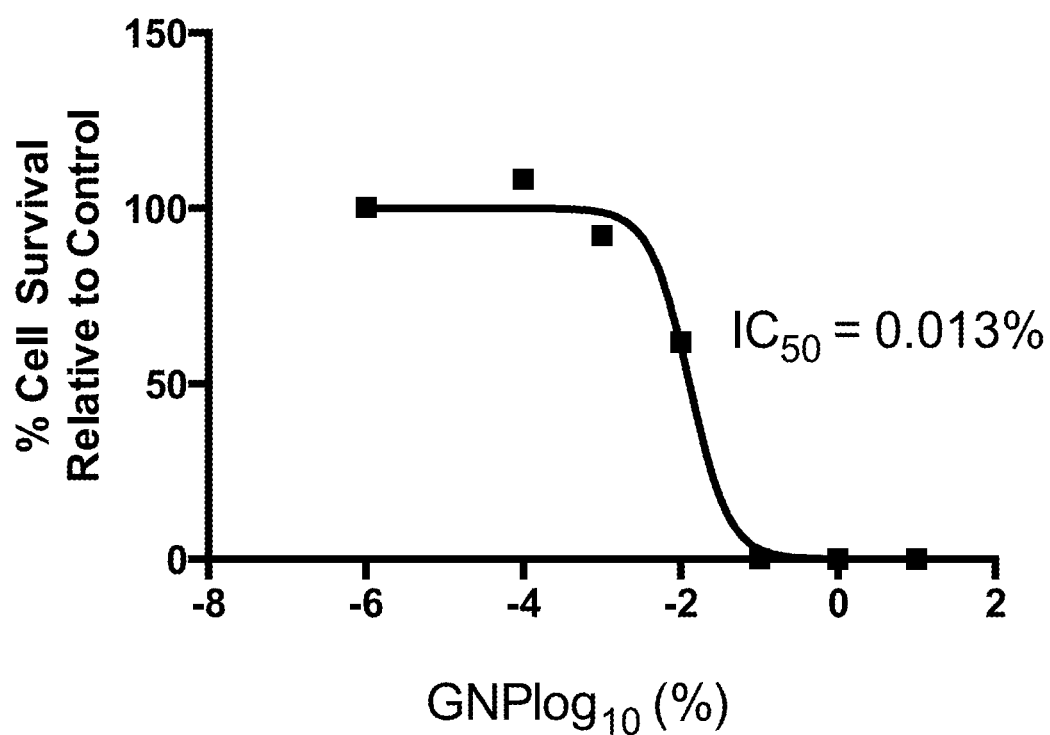
FIG. 8 is a graph depicting the concentration of an exemplary gold nanoparticle composition necessary for 50% inhibition of the proliferation of MDA-MB-231 cancer cells in vitro.

To investigate the anti-cancer effects in MDA-MB-231 cancer cells, the Alamar Blue™ assay was performed, which estimates cell viability based on the conversion of dye from blue to a pink color. Cells were exposed for 72 hours with media containing either the AuNPs in buffer alone or the AuNPs coated with the BS and CM extracts at both the regular and extra strengths. MDA-MB-231 cells showed greater sensitivity to the compositions than the MCF-7 cells, particularly using the extra strength composition ($IC_{50}$=0.013% vs. 0.04%) (FIG. 7). Both cell types exhibited comparable sensitivity to the composition at the regular strength ($IC_{50}$=0.13% vs. 0.15%) (FIG. 8).

Figure 9:
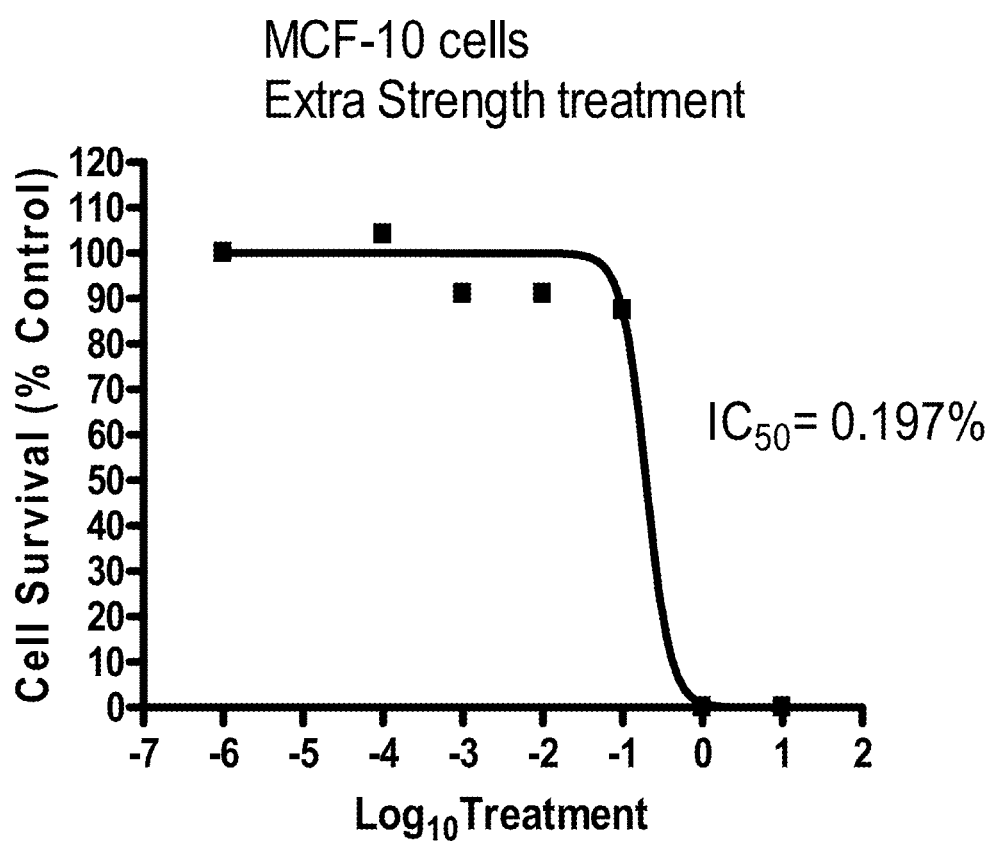
FIG. 9 is a graph depicting the concentration of an exemplary gold nanoparticle composition necessary for 50% inhibition of the proliferation of MCF-10A healthy cells in vitro.

To determine whether the cytotoxic effects of the compositions were selective for malignant cells in comparison to non-tumorigenic cells, the non-tumorigenic MCF-10A cells were exposed to the compositions at varying percentages in a similar fashion as the cancer cells. The MCF-10A cells were less susceptible to the actions of the composition, particularly using the extra strength composition ($IC_{50}$=0.19%) (FIG. 9).

Figure 10:
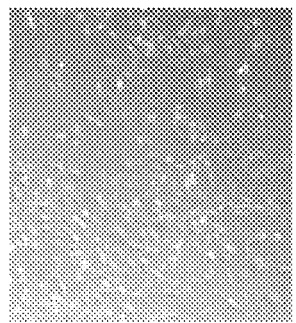
FIG. 10 depicts microscopy MDA-MB-231 cells treated in vitro with control or with different concentrations of an exemplary gold nanoparticle composition.
Figure 10:
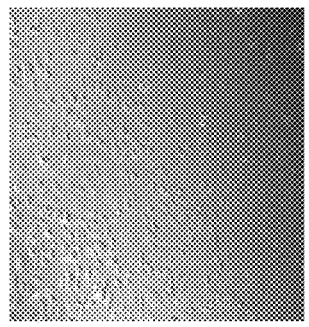
Figure 10:
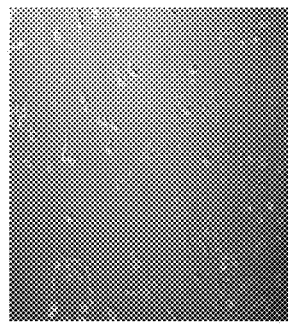
Figure 10:
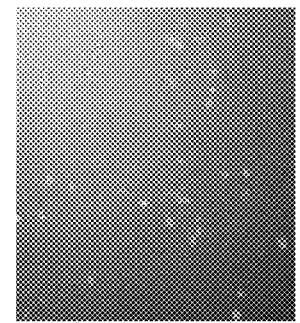
Figure 11:
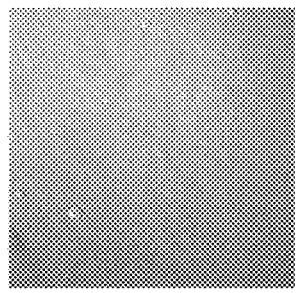
FIG. 11 depicts microscopy of MCF-7 cells treated in vitro with control or with different concentrations of an exemplary gold nanoparticle composition.
Figure 11:
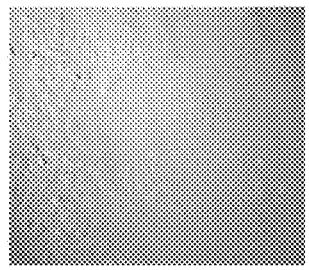
Figure 11:
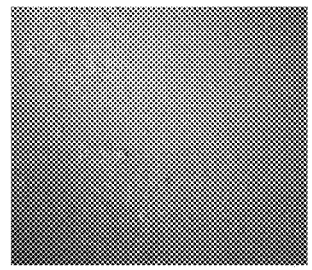
Figure 11:
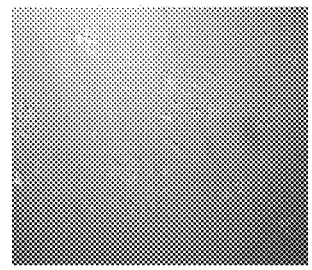
Figure 12:
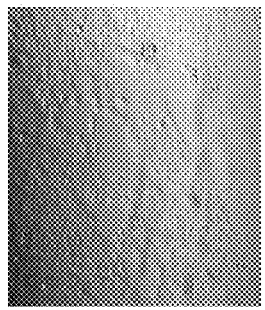
FIG. 12 depicts microscopy of MCF-10A healthy cells treated in vitro with two different concentrations of an exemplary gold nanoparticle composition.
Figure 12:
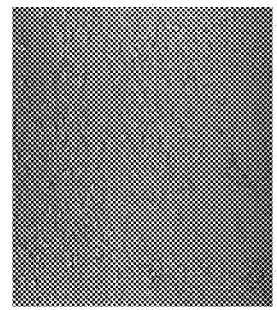

Relief contrast microscopy was used to detect morphological changes in breast cancer cells reminiscent of programmed cell death or apoptosis. MDA-MB-231 and MCF-7 cells were treated with varying percentages of the composition (0.001-1%) using both regular and extra strength compositions for 72 hours and then examined for formation of apoptotic bodies using relief contrast microscopy. Non-tumorigenic MCF-10A cells were also exposed to 0.1% of the regular and extra strength composition. No appreciable apoptotic body formation in MCF-10A cells was detected. MDA-MB-231 and MCF-7 cells, conversely, did exhibit apoptotic body formation, particularly at percentages of the respective strengths that exceeded the determined $IC_{50}$ values, as depicted in FIGS. 10-12.

The data indicate that the triple negative MDA-MB-231 cells, which bear an aggressive phenotype, responded even more favorably to the composition than the less aggressive, estrogen receptor positive, MCF-7 breast cancer cells. The diminished cytotoxicity observed when non-tumorigenic MCF-10A cells were exposed to the extra strength composition (healthy cells) suggests that this composition will offer promising treatment/therapy for patients with breast cancer cells with estrogen and progesterone receptors as well as the triple negative breast cells, with a higher potential for the more aggressive TNBCs, without causing harm to non-tumorigenic cells.

It is imperative that a capping agent be used to prevent aggregation, and the primary method of administration would be injection of Aura-Bosphora directly into the cancerous sites to reduce long circulatory times which could cause the functionalized nanoparticles to travel to or deposit in unnecessary areas of the body. Other methods of administration are contemplated including, but not limited to, intravenous and intraperitoneal injection. One approach would be to deliver Aura-Bosphora to the primary tumors as well as at the site of metastasis and its microenvironment while monitoring the prognosis through non-invasive techniques. Nanoparticle drug delivery may reduce the dosage of anti-cancer drugs with better specificity, enhanced efficacy and lower toxicities.

The benefits of the present disclosure relative to conventional systems and methods for the treatment of cancer include, but are not limited to: preferential targeting of cancerous cells; reduced toxicity toward non-cancerous cells; reduction in pain of the subject; and reduced anxiety and improved mood in the subject.

References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

The various embodiments of the systems and methods described herein are exemplary. Other variations for the systems and methods described herein are possible.

Now, therefore, the following is claimed:

1. A therapeutic composition, comprising:
   a plurality of gold nanoparticles;
   wherein surfaces of the gold nanoparticles are coated with citrate ions, frankincense and myrrh.

2. The composition of claim 1, wherein the diameter of the gold nanoparticles is less than about 30 nm.

3. The composition of claim 1, wherein the diameter of the gold nanoparticles ranges between about 10 and 20 nm.

4. The composition of claim 1, wherein the frankincense comprises an extract from *Boswellia sacra*.

5. The composition of claim 1, wherein the myrrh comprises an extract from *Commiphora myrrha*.

6. The composition of claim 1, wherein the frankincense comprises: Boswellic acid; at least one sesquiterpene; incensole acetate; alpha-pinene; limonene; myrcene; beta-phellandrene; benzene; alpha-phellandrene; 1,3,6 heptatriene; and cycloalkane.

7. The composition of claim 1, wherein the frankincense comprises Boswellic acid.

8. The composition of claim 1, wherein the myrrh comprises: furanocudesma-1, 3-diene; curzarene; nitrofurantoin; diethyl phthalate; 2-ethoxy-6-ethyl-4,4,5 trimethyl-1,3 dioxa-4 sila-2 boracylcohex-5-ene; and napthalene.

9. The composition of claim 1, wherein the myrrh comprises at least one sesquiterpene.

10. The composition of claim 3, wherein the frankincense comprises an extract from *Boswellia sacra*, and wherein the myrrh comprises an extract from *Commiphora myrrha*.

\* \* \* \* \*